United States Patent [19]

Walz et al.

[11] Patent Number: 4,840,770
[45] Date of Patent: Jun. 20, 1989

[54] ODOR CONTROL PRODUCT DISPENSER

[75] Inventors: David K. Walz, Stone Mountain; Robert D. Howerton, Decatur, both of Ga.; Andrew W. Allen, East Jordan, Mich.; Thera C. Moss; William H. Kenney, both of Cleveland, Tenn.

[73] Assignee: SECO Industries, Inc., Cleveland, Tenn.

[21] Appl. No.: 17,542

[22] Filed: Feb. 24, 1987

[51] Int. Cl.$^4$ .............................................. A61L 9/12
[52] U.S. Cl. ....................... 422/49; 239/60; 261/30; 261/DIG. 65; 422/124; 422/306
[58] Field of Search ................ 422/4, 124, 49, 305, 422/306; 239/34, 60; 261/30, DIG. 65

[56] References Cited

U.S. PATENT DOCUMENTS

| | | | |
|---|---|---|---|
| 2,585,339 | 2/1952 | Miller | 422/124 |
| 2,614,820 | 10/1952 | Boydjieff | 422/306 |
| 3,576,593 | 4/1971 | Cicirello | 422/124 |
| 3,990,848 | 11/1976 | Corris | 422/49 |
| 4,035,451 | 7/1977 | Tringali | 261/101 |
| 4,154,251 | 5/1979 | Doyel | 422/124 |
| 4,339,079 | 7/1982 | Sato et al. | 422/306 |
| 4,432,938 | 2/1984 | Meitze, Jr. | 422/49 |

Primary Examiner—Joye Woodard
Attorney, Agent, or Firm—Renner, Otto, Boisselle & Sklar

[57] ABSTRACT

Odor control product dispenser includes a cabinet having a removable front cover for directly accessing both an upper fan compartment and a lower product compartment from the front. A fan in the fan compartment draws air in through a fan shroud surrounding the fan and directs the air downwardly into the product compartment for flow across an exposed surface of the odor control product in the second compartment and subsequent discharge through air vents in the front and sides of the cabinet. The odor control product is contained in a well in one end of a disposable container. Within the well are a plurality of circumferentially spaced pinwheel type baffles that increase the turbulence of the air flowing across the product as the product evaporates to accelerate the rate of evaporation as the product loses its potency (effectiveness) with age. Also, the product shrinks away from the baffles to increase the surface area of the product exposed to the air and thus the rate of evaporation of the product as the effectiveness of the product diminishes. In the end of the container opposite the well is a battery compartment containing a battery which provides the power source for driving the fan motor. Cooperating surfaces on the container and dispenser properly orient the battery within the product compartment and maintain the battery terminals in contact with motor contact strips in the second compartment.

45 Claims, 4 Drawing Sheets

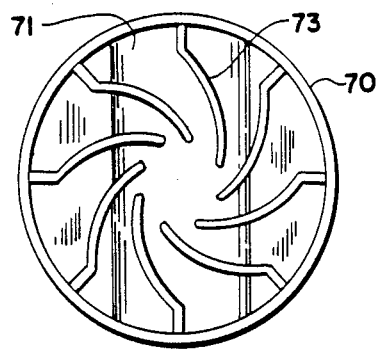
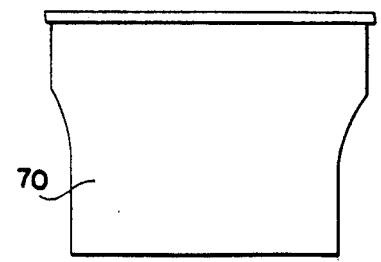
FIG. 11    FIG. 9
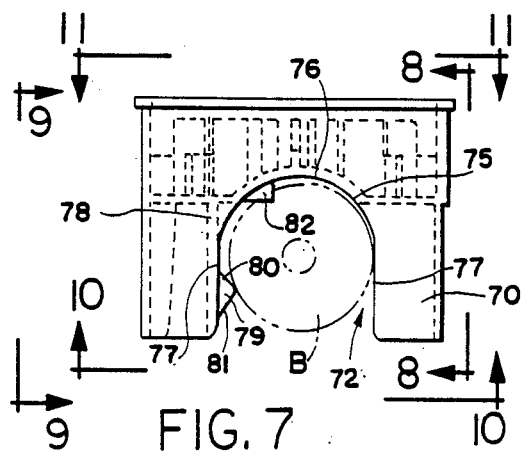
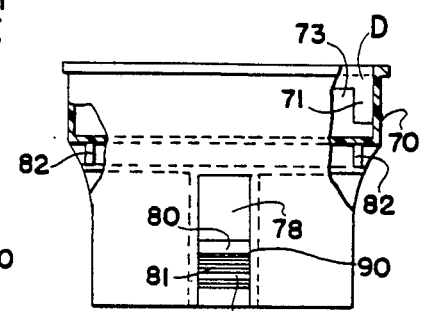
FIG. 7    FIG. 8
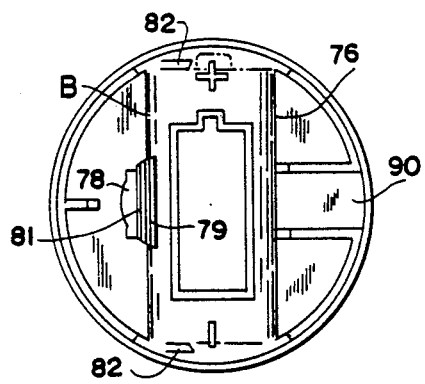
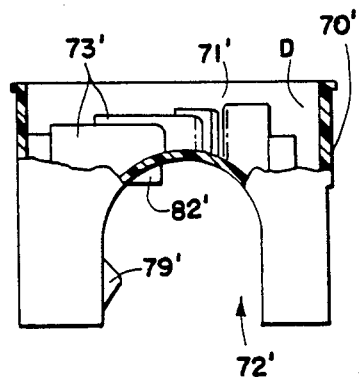
FIG. 10    FIG. 12

4,840,770

ODOR CONTROL PRODUCT DISPENSER

BACKGROUND OF THE INVENTION

This invention relates generally as indicated to an odor control product dispenser, including a cabinet having isolated compartments for housing a fan and a disposable container for housing both the odor control product and a battery for powering the fan. The fan induces a flow of air through the cabinet and across the exposed surface of the odor control product to aid in its evaporation and distribution throughout the environment where the dispenser is located. While such a dispenser is particularly suited for use in dispensing air fresheners in restrooms and locker rooms and the like, it should be understood that such a dispenser may be installed anywhere that it is desired to freshen or otherwise treat the air.

It is generally known from U.S. Pat. No. 3,990,848 to provide a system for inducing air flow past a gel type odor control product to aid in the distribution of the product in vaporized form into the environment to be treated. However, there is still a need for a dispenser that more effectively maintains a substantially constant level of fragrance within the room as the potency of the fragrance diminishes with time. Also, there is a need for a dispenser that more efficiently directs a precise volume of air across the odor control product, and has provision for adjusting the air flow to allow tailoring the dispenser output to a particular application.

Furthermore, there is a need for a disposable container for the odor control product which not only exposes a relatively large surface of the product to the air flowing through the dispenser, but also provides for the increase of such surface area and increased turbulence of the air passing over the product as the product is used up to accelerate the rate of vaporization of the remaining product to maintain a substantially constant level of fragrance as the potency of the fragrance diminishes with time.

In addition, there is need for such a disposable container that incorporates the odor control product in the top portion and a battery for powering the fan in the bottom portion for ease of replacement of the odor control product and battery as a unit, with provision for keying the container into the cabinet to ensure that the battery is properly oriented with respect to the fan motor contact strips and is prevented from riding up over the contact strips.

Also, there is a need for a dispenser of the type described which is relatively compact and substantially modular in construction, making it easier to service and repair without the use of any tools or the like.

SUMMARY OF THE INVENTION

With the foregoing in mind, it is a principal object of this invention to provide an odor control product dispenser that more effectively maintains a relatively constant level of fragrance within a room over a substantial period of time.

Another object is to provide a novel disposable container for such dispenser including a well in the top for the odor control product and a battery receiving compartment in the bottom which provides the power source for the dispenser fan.

Still another object is to provide cooperating surfaces on the dispenser cabinet and disposable container for properly orienting the container within the dispenser so that the battery terminals properly engage contact strips within the cabinet to provide power to the dispenser fan.

A further object is to provide for the increased turbulence of the air passing over the odor control product within the dispenser to accelerate the vaporization (evaporation) of the product as the potency of the fragrance diminishes with time.

Still another object is to provide for the progressive increase in the surface area of the odor control product exposed to the air passing thereover to accelerate the vaporization of the product as the product is used up over time.

A further object is to provide for the adjustment of the air flow through the dispenser and across the odor control product to allow tailoring of the fragrance strength to a particular application.

Yet another object is to provide a dispenser of the type described which is relatively compact and modular in construction, making it easier to service and repair without the use of any tools.

These and other objects of the present invention may be achieved by providing the dispenser cabinet with a removable front cover for directly accessing both a fan compartment and product compartment from the front of the dispenser. Within the fan compartment is a motor driven fan that draws air in through axial inlet openings in a fan shroud surrounding the fan and directs the air downwardly through a radial outlet in the bottom of the fan shroud to the product compartment and then back out through air vents in the front and sides of the cabinet. The product compartment is adapted to receive a disposable container having a well in the top thereof containing the odor control product in gel form and a battery compartment in the bottom thereof which provides the power source for driving the fan motor. Preferably, there are a plurality of circumferentially spaced pinwheel type baffles in the well that become increasingly exposed to the air flow across the product as the product is used up to increase the turbulence of the air flow passing over the product, thus accelerating the evaporation of the product as the product loses its potency with age. At the same time, the surface of the product exposed to the air flow increases due to the shrinking of the product away from the baffles and sides of the container so that the amount of vaporization of the product increases with time to provide a substantially constant fragrance release from the dispenser. The relative height of the baffles may also be varied so that the number of baffles exposed to the air increases with time to increase the turbulence of the air flow passing over the product.

Cooperating surfaces may be provided on the disposable container and dispenser cabinet for proper orientation of the battery within the product compartment and to maintain the battery terminals in contact with the fan motor contact strips within the dispenser. Also, an air regulator may be provided on the front of the fan shroud for adjusting the amount of air intake into the fan to tailor the output for a specific application.

To the accomplishment of the foregoing and related ends, the invention, then, comprises the features hereinafter fully described and particularly pointed out in the claims, the following description and accompanying drawings setting forth in detail certain illustrative embodiments of the invention, these being indicative, however, of but several of the various ways in which the principles of the invention may be employed.

BRIEF DESCRIPTION OF THE DRAWINGS

In the annexed drawings:

FIG. 7 is an enlarged side elevation view of a disposable container for the dispenser as seen from one side thereof;

FIG. 8 is another side elevation view, partially broken away, of the container of FIG. 7 as seen from the plane of the line 8—8 which is offset approximately 90° from that shown in FIG. 7;

FIG. 9 is another side elevation view of the disposable container of FIG. 7 as seen from the plane of the line 9—9 thereof which is directly opposite the side shown in FIG. 8;

FIG. 10 is a bottom plan view of the disposable container of FIG. 7 as seen from the plane of the line 10—10 thereof;

FIG. 11 is a top plan view of the disposable container of FIG. 7 as seen from the plane of the line 11—11 thereof; and FIG. 12 is an enlarged side elevation view, similar to FIG. 7, of a modified form of disposable container, with portions broken away to show baffles of varying heights within the top portion of the container.

DETAILED DESCRIPTION OF THE PREFERRED EMBODIMENTS

Figure 1:
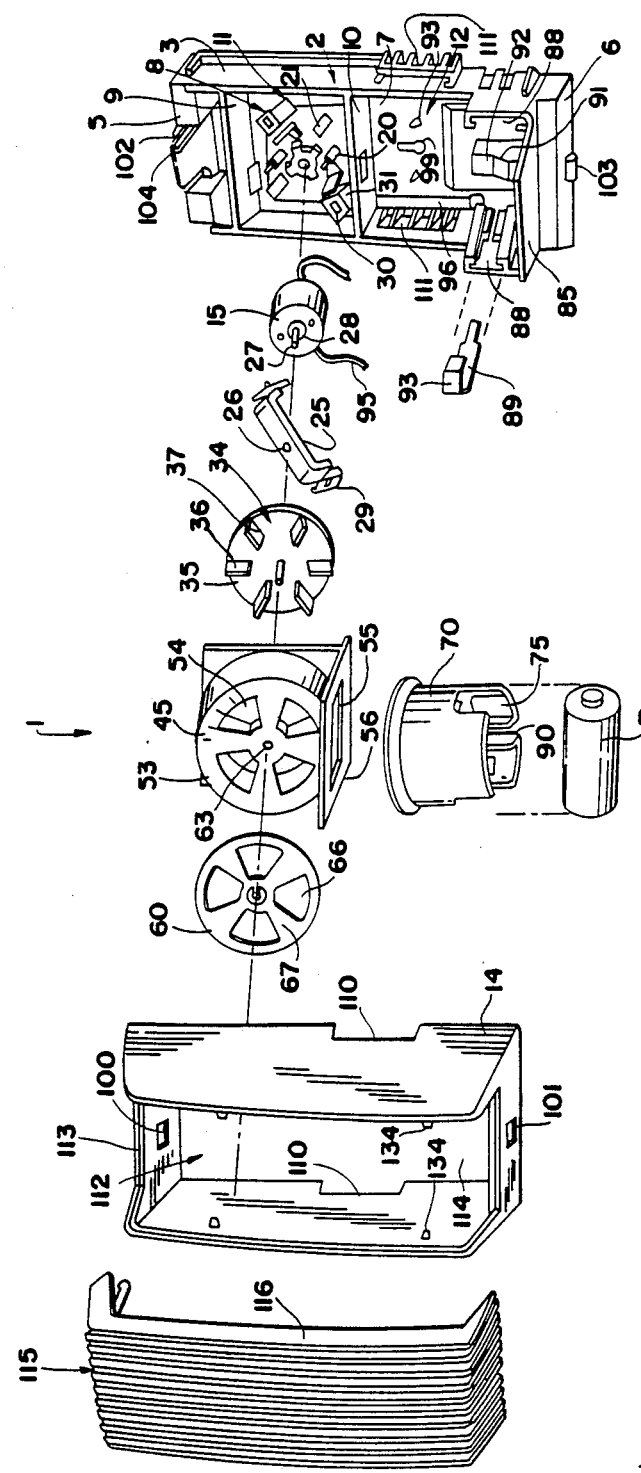
FIG. 1 is an exploded perspective view showing the various parts of one form of dispenser apparatus in accordance with this invention in disassembled form.
Figure 2:
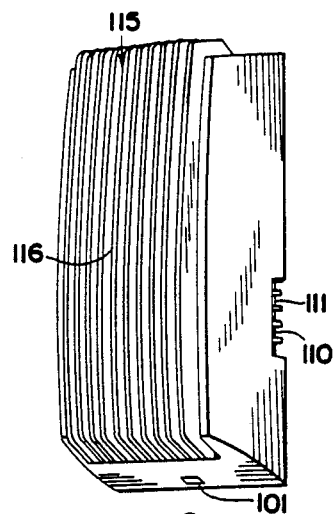
FIG. 2 is a perspective view of the dispenser of FIG. 1 in assembled condition.
Figure 4:
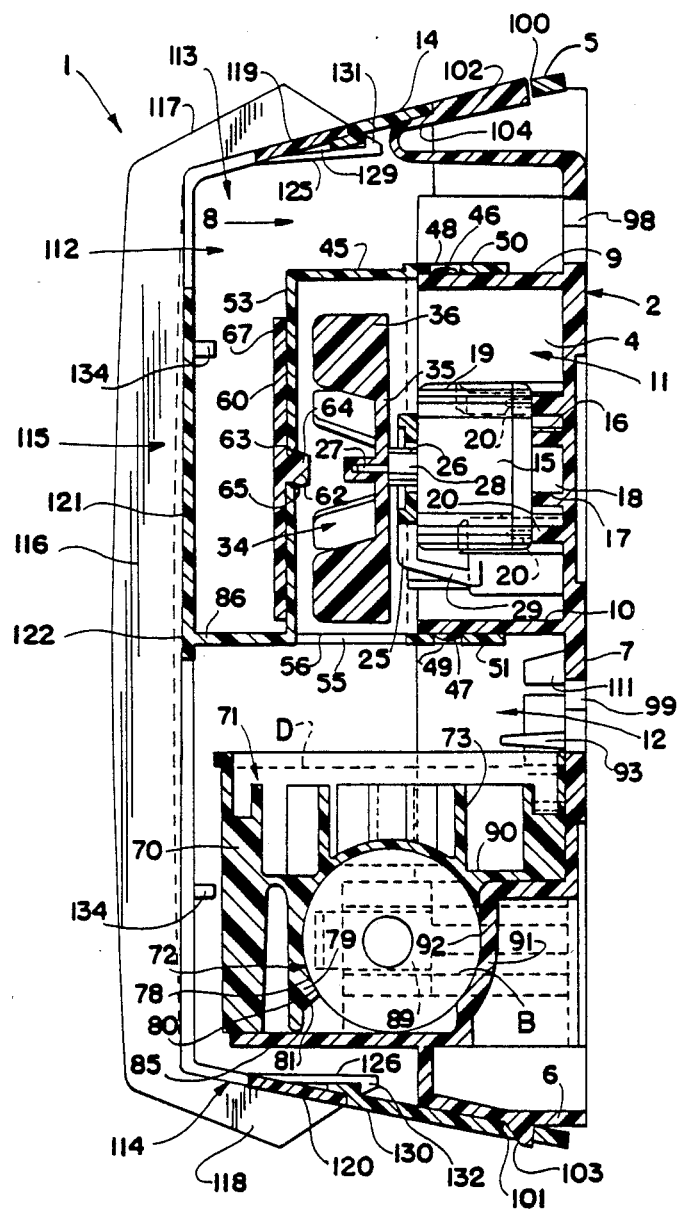
FIG. 4 is a still further enlarged longitudinal section through the dispenser apparatus of FIG. 3, taken generally along the plane of the line 4—4 thereof.

Referring now in detail to the drawings, and initially to FIGS. 1 and 4, a referred form of odor control product dispenser in accordance with this invention is generally indicated by the reference numeral 1, and includes a cabinet or main housing 2 having a pair of side walls 3, 4 and top and bottom walls 5, 6 and a back wall 7 and open front 8 adapted to be covered by a removable cover 14. Within the housing 2 are a pair of spaced apart partitions 9, 10 extending transversely between the side walls 3, 4 and from the back wall 7 toward the open front 8, thus defining upper and lower compartments 11, 12 which are isolated from each other within the housing. The upper compartment 11 is a motor compartment for mounting of a fan motor 15 and associated fan 34 therein.

Figure 6:
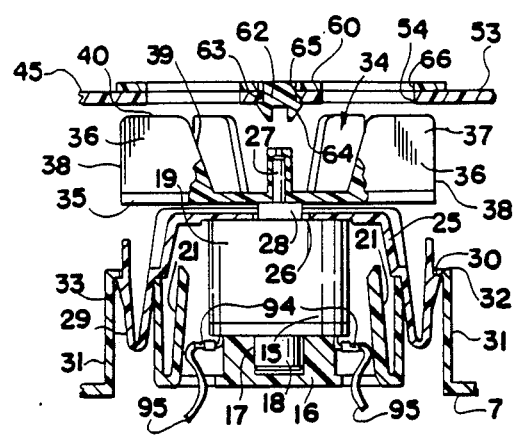
FIG. 6 is a further enlarged fragmentary longitudinal section through the fan shroud, fan and dispenser fan motor mount of the dispenser of FIG. 5, taken generally along the plane of the line 6—6 thereof.
Figure 3:
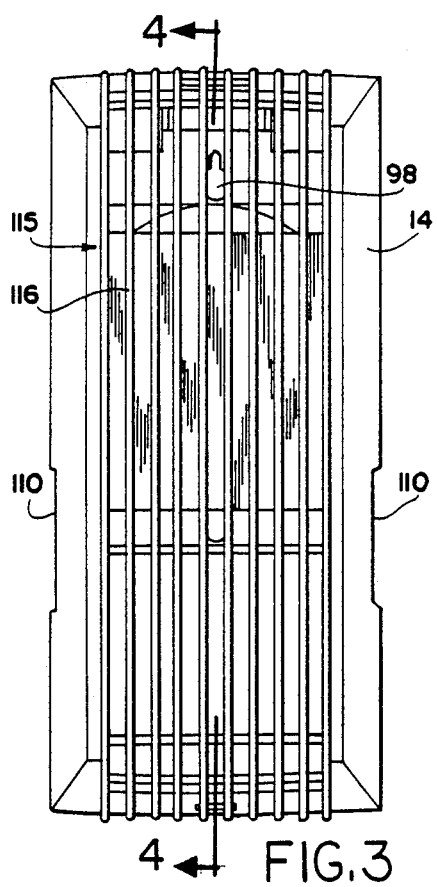
FIG. 3 is an enlarged front elevation view of the dispenser of FIG. 1.

To properly orient and locate the fan motor 15 within the motor compartment 11, a central boss 16 may be provided on the back wall of the compartment, such boss 16 having a central well or recess 17 for close sliding receipt of a cylindrical extension 18 on the back end of the motor housing 19 as shown in FIGS. 4 and 6. Also, a pair of upstanding pins 20 may be provided on such housing back wall 7 for receipt in locating holes in the back end of the motor housing. In addition, a plurality of forwardly extending tabs 21 may be provided on such back wall in circumferentially spaced relation around the boss 16 to help guide the motor into place within the compartment 11. When thus properly positioned, the fan motor 15 may be releasably clamped in place against the back wall 7 as by means of a motor support clip 25 which has a center hole 26 therethrough for insertion over the motor shaft 27 and shaft bearing 28 and a pair of rearwardly extending spring-like fingers 29 at opposite ends thereof adapted to be inserted into the open ends 30 of a pair of upstanding posts 31 extending forwardly from the back wall 7. Each post opening 30 has a flange or lip 32 along one edge (see FIG. 6) which is adapted to be engaged by a shoulder 33 on the clip fingers when inserted in such openings to releasably lock the ends of the motor support clips to the posts. In such assembled condition, the motor shaft 27 extends forwardly beyond the front edges of the side walls 3, 4 and partitions 9, 10 for mounting of the centrifugal fan 34 thereon radially outwardly of such edges as seen in FIG. 4.

Referring further to FIG. 4, and also to FIGS. 1 and 6, the fan 34 is a centrifugal fan including an annular disk 35 having a plurality of circumferentially spaced radially extending fan blades 36 on the front face thereof. In the embodiment shown, there are six such fan blades 36, each spaced approximately 60° apart, and having substantially parallel flat sides 37 extending substantially perpendicular from the front face of the disk 35. The radial outer edges 38 of the fan blades 36 are also desirably substantially perpendicular to the front face of the disk 35, whereas the radial inner edges 39 desirable slope outwardly at an angle, for example, of approximately 74° from the front of the disk. The top edges 40 of the blades 36, on the other hand, are desirably substantially straight and parallel to the front face of the disk, except at the corners, which are desirably slightly rounded as shown.

Figure 5:
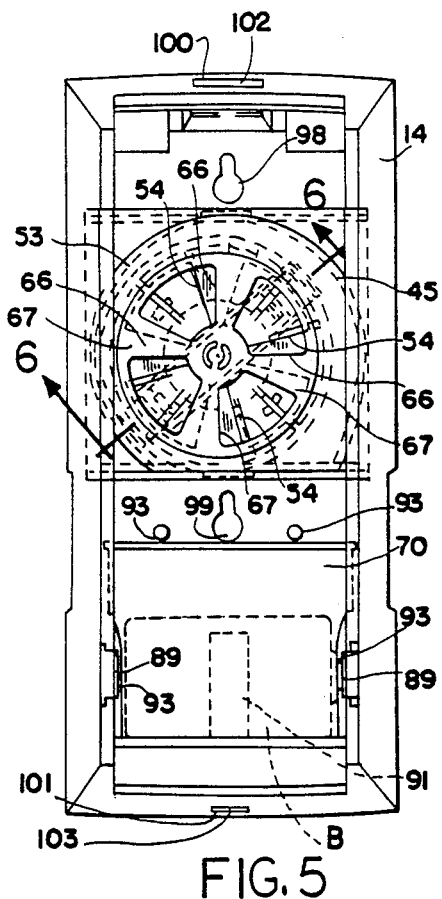
FIG. 5 is an enlarged front elevation view of the dispenser similar to FIG. 3, but showing the front grill removed.

Surrounding the fan 34 is a fan shroud 45 which may be releasably attached to the dispenser housing 2 as by providing raised ribs 46 and 47 on the respective top and bottom surfaces of the upper and lower partitions 9 and 10 for snapping engagement into slots 48 and 49 in a pair of rearwardly extending flanges 50 and 51 on the fan shroud (see FIG. 4). The fan shroud has a front facing end wall 53 with a plurality of circumferentially spaced axial inlet openings 54 therethrough for the passage of air which is drawn into the center of the fan 34 during rotation of the fan in a counterclockwise direction as seen in FIG. 5 and forced radially outwardly for discharge through a radial outlet opening 55 in the bottom wall 56 of the fan shroud into the lower compartment 12 and then out into the atmosphere as described hereafter. The axial inlet openings 54 and fan axis are desirably eccentrically offset to the left of the center axis of the shroud as seen in FIG. 5 to reduce the air flow area of the fan as the air flow approaches the air discharge opening 55. This produces a venturi effect within the fan that boosts the air speed as the air is discharged into the lower compartment 12, increasing the fan efficiency and delivering more air to the lower compartment at slower fan speed, thus preserving battery power and prolonging battery life.

An air regulator 60 may be attached to the front end wall 53 of the fan shroud 45 for regulating the amount of air flow through the axial inlet openings 54 therein. As best seen in FIGS. 4–6, such air regulator is in the shape of a disk having a central hub portion 62 extending through an opening 63 in the front end wall 53 of the fan shroud 45 for rotatably mounting the regulator disk to the fan shroud. The hub portion 62 is desirably slotted across the diameter thereof to provide a pair of spring-like fingers 64 with ribs 65 thereon which provide a snap connection between the regulator disk and fan shroud.

Preferably, the regulator disk has the same number, size and location of pie-shape openings 66 therethrough as in the fan shroud, whereby when the regulator disk 60 is rotated so that the openings 66, 54 are in direct alignment with each other, the regulator disk will not limit in any way the air flow through the openings 54. However, as the regulator disk is progressively rotated out of alignment, the inlet openings 54 in the fan shroud are progressively closed by the web-like members 67 of the regulator intermediate the openings 66 to correspondingly reduce the amount of air flow permitted therethrough. On the other hand, it is preferred that the openings 54 and 66 are each larger than the respective web-like members 67, for example, approximately twice as large, whereby the air flow adjustment will always remain at least partially open to protect the battery against premature burn-out. Also, suitable indicia may be provided on the front face of the fan shroud and air regulator to assist in selecting the desired position of the air regulator relative to the fan shroud for regulating the air flow therethrough.

The lower compartment 12 is adapted to receive a disposable container 70 which, as best seen in FIGS. 4, 7, 10 and 11, has a well 71 in the top thereof for receipt of an odor control product D, preferably in gel form, and a battery compartment 72 in the bottom thereof for receipt of a battery B used to power the fan motor 15. The gel forms an ideal carrier for the fragrance, in that it cannot spill, and also prevents premature fragrance evaporation. Moreover, an air-tight seal may be provided across the top of the container to keep the product at full strength until ready for use. Of course, the seal must be removed before the disposable container is inserted into the dispenser to be effective.

Once the seal is removed, the fragrance nevertheless progressively loses its potency (effectiveness) with age. To compensate for that, a plurality of circumferentially spaced pinwheel type baffles 73 are desirably provided in the well. Each baffle 73 is desirably curved over a major portion of its length, and extends generally radially inwardly from the annular side wall of the well but preferably at a slight angle toward the next succeeding baffle so that the spacing between adjacent baffles becomes progressively smaller toward the axial center of the well (see FIG. 11) for a purpose to be subsequently described. Also such baffles desirably extend generally vertically upward from the bottom wall of the well for a substantial portion of the height thereof, but terminate short of the open top thereof as shown in FIGS. 4 and 8 for reasons described hereafter.

Initially, when the well 71 is substantially completely filled with the gel-like odor control product D, the baffles 73 are desirably completely covered by the product. However, as the product gradually evaporates during use, the baffles become progressively exposed to the air. This has the advantage that the baffles will cause the turbulence of the air flowing over the exposed surface of the product D to increase as the product is used up to increase the rate of vaporization of the product with time, which is important in order to maintain approximately the same level of effectiveness of the fragrance because the fragrance progressively loses its potency (effectiveness) with age as aforesaid. Also, by shaping the baffles so that they progressively slope toward each other toward the center of the well in the manner previously described, the velocity of the air flowing over the product is increased to further increase the air turbulence and thus the rate of vaporization of the product with age.

The provision of baffles has the further advantage that as the product evaporates, in time the product will shrink away from the baffles and container side wall to increase the surface area of the product exposed to the air flow to further increase the rate of vaporization of the product.

In FIGS. 7 and 8, the baffles 73 are all shown as being of substantially the same height. However, it should be understood that baffles 73' of varying heights may be provided as shown in FIG. 12 to progressively increase the number of baffles exposed to the air as the product is used up also to correspondingly increase the air turbulence and surface area of the product exposed to the air and thus the rate of vaporization of the product with time. Otherwise, the details of construction and operation of the disposable container 70' shown in FIG. 12 are substantially the same as the disposable container 70 previously described, and the same reference numerals followed by a prime symbol are used to designate like parts.

The battery compartment 72 on the bottom side of the disposable container 70 is desirable in the shape of a generally inverted U-shaped slot 75 extending transversely from one side of the container to the other and completely open at the bottom for insertion of the battery sideways therein. The top wall 76 and upper (inner) side edges of the slot 75 are desirably generally rounded to match the rounded contour of the battery B, which may be a conventional 1.5 volt D-cell battery. The remaining length of the sides 77 of the slot are substantially straight for ease of insertion of the battery into the slot through the open bottom. On one side of the slot 75 is a spring-like finger 78 having a cam-like projection 79 on the side facing the interior of the slot for frictionally retaining the battery within the slot. The one side of the slot is relieved behind the finger 78 by a recessed portion to permit flexing of the finger away from the slot and into the recessed portion. The cam-like projection 79 is desirably generally triangular shape in cross-section, with oppositely tapering side faces 80, 81 to facilitate camming of the finger out of the way both when the battery is pushed up into the slot from the open bottom and when the battery is pulled out of the slot.

The top wall 76 of the battery slot 75 may be marked with suitable indicia such as polarity symbols at one or both ends thereof as shown in FIG. 10 to make certain that the battery is always correctly oriented in the slot. Also, battery holder tabs or stops 82 may be provided at the ends of the slot to prevent the battery from sliding sideways out of the slot as shown in FIGS. 7, 8 and 10.

At the bottom of the product compartment 12 within the dispenser cabinet 2 is a shelf 85 that extends forwardly beyond the front edges of the cabinet for supporting the disposable container 70 thereon in substantial vertical alignment with the air discharge slot 55 in the fan shroud 45. A flange 86 also desirably extends from the bottom wall 56 of the fan shroud forwardly of the bottom shelf 85 for maintaining the front cover 14 in spaced relation from the shroud and isolating the fan compartment 11 and product compartment 12 from each other.

On opposite sides of the lower compartment 12 adjacent the upper surface of the bottom shelf 85 are a pair of slots 88 extending from front to rear in which are mounted battery contact strips 89 that are engaged by the battery terminals at the ends of the battery when the disposable container 70 is properly inserted into the product compartment. To ensure proper orientation of the battery within the product compartment, the container 70 is desirably keyed into the cabinet. For that purpose, the side wall portion of the container opposite the spring-like finger 78 has a radial slot 90 (see FIGS. 1, 4, 8 and 10) extending therethrough in a direction generally perpendicular to and intersecting the battery receiving slot 75 intermediate its opposite ends. This radial slot 90 is adapted to receive a projection 91 on the back wall 7 of the product compartment 12 for properly aligning the battery terminals with the battery contact strips 89 in the housing slots 88. The forward end wall 92 of the projection 91 desirably has a partially rounded contour as shown in FIGS. 1 and 4 to provide additional support for the battery when the container is fully inserted into the housing. Also, one or more pins 93 may be provided on the back wall of the cabinet in vertically spaced relation from the bottom shelf 85 a distance slightly greater than the overall height of the container 70 as shown in FIGS. 4 and 5 to prevent the battery terminals from riding up over the contact strips 89.

The forward ends of the battery contact strips 89 are desirably bent back on themselves to provide spring contacts 93 which frictionally contact the battery terminals as shown in FIG. 5. The rear ends of the battery contact strips are in turn connected to the fan motor terminals 94 (see FIG. 6) by wiring 95 which is desirably routed behind the dispenser cabinet so as not to interfere with the disposable container placement or servicing of the dispenser. The wiring may be received in wire guides 96 extending along the back wall 7 of the dispenser housing and connected to the fan motor terminals 94 as by means of quick disconnect connectors.

When the disposable container 70 is properly inserted in the product compartment 12 with the battery terminals in contact with the motor contact strips 89 as previously described, the motor 15 will operate continuously to continuously drive the fan 34 for the life of the battery, which need not be greater than the time it takes to vaporize the odor control product within the container. This has the advantage that both the product and battery can be installed and replaced at the same time as a unit, thus assuring that an old battery is not left in by mistake. Also, the battery is desirably pre-installed in the disposable container to ensure against improper placement. However, it will be apparent that if either the battery or odor control product is used up at a substantially different rate, one could be replaced without replacing the other if desired.

The front cover 14 for the cabinet 2 is removable from the front to facilitate insertion and removal of the disposable container 7 from the front while the dispenser is mounted on a wall or used as a free-standing unit on a shelf or desk top or the like. When mounted on a wall, the cabinet is oriented with the fan compartment 11 above the product compartment 12 as shown in FIGS. 1, 4 and 5. To facilitate such wall mounting, two mounting slots 98, 99 may e provided in the back wall of the cabinet, one such mounting slot 98 being provided above the upper partition 9, and the other mounting slot 99 being provided below the lower partition 10. Alternatively, built-in self-adhesive strips may be provided for the purpose.

The front cover 14 may be retained on the dispenser cabinet as by providing notches or slots 100 or 101 in the top and bottom walls of the cover for engagement by tabs or projections 102 and 103 on the top and bottom walls of the cabinet. The top projection 102 is desirably supported by a spring member 104 to facilitate disengagement of the cover from the cabinet by pressing down on the top projection 102. The entire cabinet including the spring member 104 may be molded as an integral unit out of a suitable plastic material. Moreover, the spring member 104 desirably extends at a slight upward angle from front to rear to facilitate camming of the cover onto the cabinet after engaging the bottom slot 101 over the bottom projection 103 on the bottom wall of the cabinet.

The top and bottom walls and sides of the cover 14 desirably completely surround the cabinet 2 except along the back edge in the region of the product compartment 12 which desirably has notches 110 therein to permit venting of the product compartment along the back sides through a series of side vents III in the cabinet.

The front 112 of the dispenser cover 14 and portions 113, 114 of the top and bottom walls adjacent the front are desirably left open for receipt of a grill 115 formed as by a plurality of laterally spaced louvers 116 extending the full length of the cover and having inturned ends 117, 118 extending within the top and bottom openings 113 114. The louvers 116 may be connected together by plastic cross members 119, 120, 121 on the inner surfaces of the louvers at the ends, and in an area intermediate the ends.

The intermediate cross member 121 is adapted to engage the front edge 122 of the outturned flange 86 on the bottom of the fan shroud 45 when the cover 14 is properly mounted in place on the cabinet 2, to isolate the product compartment 12 from the fan compartment 11 and cause the air flow to the fan 34 to be through the top portions of the louvers 116 above the intermediate cross member and the air discharge from the product compartment 12 to be through the bottom portions of the louvers below the intermediate cross member and through the side vents 111 to distribute the air directly into the room and along the wall for more complete odor control.

The front grill 115 may be removably attached to the front cover 14 by providing a pair of flexible fingers 125, 126 on the undersides of the cross members 19, 120 at the ends of the louvers 116. The cross members 119, 120 and associated fingers 125, 126 cooperate with each other to engage opposite sides of inwardly extending lips or flanges 129, 130 on the front edges of the top and bottom walls of the front cover 14. Also, the fingers 125, 126 may have outwardly facing shoulders 131, 132 thereon adapted to engage the back sides of the inturned lips to provide a snap connection therebetween. The intermediate portions of the louvers 116 may rest up against projections 134 of the inner surfaces of the cover side walls adjacent the front edges thereof as shown in FIGS. 1 and 4.

From the foregoing, it will now be apparent that the disposable container for the odor control product dispenser of the present invention incorporates both the odor control product and battery in a single unit for ease of replacement. The container includes a simple and effective means for maintaining the level of effectiveness of the fragrance of the odor control product even though its potency diminishes with age by progressively increasing the rate of vaporization of the odor control product as the odor control product is used up. Also, the container is desirably keyed into the cabinet so that it is virtually impossible to put the battery in backwards, and the battery is located below the fan motor to keep potential battery corrosion from affecting any critical dispenser components.

Furthermore, the dispenser is quite compact and may readily be mounted on the wall using screws or built-in self-adhesive strips, or used as a free-standing unit on shelves or desk tops and the like. Also, the dispenser is desirably completely modular in construction, making it easy to service and replace or repair the various component parts including the fan motor without the need for any tools and the like.

Although the invention has been shown and described with respect to certain preferred embodiments, it is obvious that equivalent alterations and modifications will occur to others skilled in the art upon the reading and understanding of the specification. The present invention includes all such equivalent alterations and modifications and is limited only by the scope of the claims.

What is claimed is:

1. Odor control product dispenser apparatus comprising a cabinet including a first compartment containing a centrifugal fan and motor, a second compartment juxtaposed to said first compartment and containing a disposable container means, first and second vent means for respectively venting said first and second compartments to the atmosphere, a shroud surrounding said fan, said shroud having axial inlet openings through which air is drawn by said fan through said first vent means and radial discharge opening means through which air is forced radially outwardly by said fan into said second compartment for flow past the disposable container means in said second compartment and discharged through said second vent means, said disposable container means having a well in one end containing odor control product means, said well having an open top exposing said odor control product means to the air flowing through said second compartment, and support means within said second compartment for supporting said container means with said open top of said well facing said radial discharge opening means and in substantial axial alignment therewith, whereby substantially all of the air entering said second compartment through said radial discharge opening means flows past said odor control product means prior to being discharged through said second vent means.

2. The dispenser apparatus of claim 1 wherein said cabinet includes a back wall having a partition extending forwardly therefrom dividing said cabinet into said first and second compartments, and said support means comprises a bottom shelf within said second compartment spaced from said partition for supporting said container means in said second compartment with said open top of said well facing said radial discharge opening means a predetermined distance from said radial discharge opening means.

3. The dispenser apparatus of claim 2 further comprising a battery compartment in another end of said container means opposite said well containing a battery, said battery having terminals at opposite ends thereof, said battery compartment being open at opposite ends thereof exposing said battery terminals to said second compartment, and said second compartment having contact strips for engaging said battery terminals when said container means is supported in said second compartment, and wire means connecting said contact strips to said motor.

4. The dispenser apparatus of claim 3 wherein said battery compartment is formed by a transverse slot in said another end of said container means opposite said well, said transverse slot having a length extending from one side of said container means to a second side of said container means opposite said one side said transverse slot having an opening along said length for insertion of said battery lengthwise into said slot with said battery terminals exposed at the opposite ends of said slot for engagement with said contact strips, and retainer means on said container means for releasably retaining said battery in said slot.

5. The dispenser apparatus of claim 4 further comprising tab means on said container means overlapping the opposite ends of said slot to prevent said battery from sliding sideways out of said slot.

6. The dispenser apparatus of claim 3 wherein said container means and said cabinet comprise means for keying said container means within said second compartment to locate said container means in a position in which said battery terminals are in proper alignment with said contact strips.

7. The dispenser apparatus of claim 6 wherein said means for keying comprises a projection on said back wall of said cabinet extending forwardly into said second compartment, and a radial slot in said another end of said container means opposite said well extending generally perpendicular to said transverse slot, said projection being engageable in said radial slot to orient said container means within said second compartment.

8. The dispenser apparatus of claim 7 wherein said radial slot intersects said transverse slot intermediate the opposite ends thereof, and said projection has a forward end with a partially rounded contour extending into said transverse slot for supporting said battery in said transverse slot.

9. The dispenser apparatus of claim 4 wherein said cabinet comprises means for preventing movement of said container means perpendicular to said support means thus preventing said battery terminals from riding up over said contact strips when said container means is inserted in said second compartment.

10. The dispenser apparatus of claim 9 wherein said means for preventing said battery terminals from riding up over said contact strips comprises pin means extending from said back wall of said cabinet forwardly within said second compartment, said pin being spaced from said bottom shelf a distance approximately equal to the overall length of said container means, said pin means overlapping said one end of said container means when said container means is inserted in said second compartment.

11. The dispenser apparatus of claim 1 wherein said well has an annular side wall and bottom wall, and a plurality of circumferentially spaced baffles extend generally radially inwardly from said side wall and vertically upwardly from said bottom wall toward said open top of said well.

12. Odor control product dispenser apparatus comprising a cabinet including a back wall having a partition extending forwardly therefrom intermediate the length of said back wall dividing said cabinet into first and second compartments, said first compartment containing a centrifugal fan and motor assembly, first and second vent means for respectively venting said first and second compartments to the atmosphere, a shroud surrounding said fan, said shroud having axial inlet openings through which air is drawn by said fan through said first vent means and radial discharge opening means for directing substantially all of the air that is forced radially outwardly by said fan into said second compartment, support means within said second compartment for supporting odor control product means for exposure to the air flowing through said second compartment prior to discharge through said second vent means, said cabinet including an open front, and a front cover extending over said open front said first and second vent means comprising a grill on said front cover for venting said first and second compartments to the atmosphere through said grill said grill being removable from said front cover, and means on said grill and front cover providing a snap connection between said grill and front cover to permit attachment and removal of said grill without the use of any tools.

13. Odor control product dispenser apparatus comprising a cabinet including a back wall having a partition extending forwardly therefrom intermediate the length of said back wall dividing said cabinet into first and second compartments, first and second vent means for respectively venting said first and second compartments to the atmosphere, passage means between said first and second compartments, fan means in said first compartment for drawing air through said first vent means and discharging such air through said passage means into said second compartment and out through said second vent means, and container means in said second compartment containing odor control product means, said container means having an open top exposing said odor control product means to the air flowing through said second compartment prior to discharge through said second vent means, and support means within said second compartment for supporting said container means with said open top facing said passage means and in substantial alignment therewith, whereby substantially all of the air entering said second compartment through said passage means flows past said odor control product means prior to being discharged through said second vent means.

14. The dispenser apparatus of claim 13 wherein said container means includes a well in one end containing said odor control product means and a battery compartment in another end containing a battery, said battery having terminals at opposite ends, said battery compartment having opening means exposing said battery terminals to said second compartment, and said second compartment having contact strips for engaging said battery terminals when said container means is supported in said second compartment, and wire means connecting said contact strips to said fan means.

15. The dispenser apparatus of claim 14 wherein said battery compartment is formed by a transverse slot in said another end of said container means, said transverse slot having a length extending from one side of said container means to a second side of said container opposite said one side, said transverse slot being open along said length for insertion of said battery lengthwise into said transverse slot with said battery terminals exposed at the opposite ends of said slot for engagement with said contact strips, and retainer means on said container means for releasably retaining said battery in said slot.

16. The dispenser apparatus of claim 15 further comprising tab means on said container means overlapping said opposite ends of said slot to prevent said battery from sliding sideways out of said slot.

17. The dispenser apparatus of claim 15 further comprising orienting means on said container means and said cabinet for orienting said container means within said second compartment to ensure contact between said contact strips and said battery terminals.

18. The dispenser apparatus of claim 17 wherein said orienting means comprises a projection on said back wall of said cabinet extending forwardly into said second compartment, and a radial slot in said another end of said container means for receipt of said projection, said radial slot extending generally perpendicular to said transverse slot.

19. The dispenser apparatus of claim 18 wherein said radial slot intersects said transverse slot intermediate the opposite ends thereof, and said projection has a partially rounded forward end wall extending into said transverse slot for supporting said battery in said transverse slot.

20. The dispenser apparatus of claim 18 further comprising pin means extending forwardly from said back wall into said second compartment, said pin means closely overlying said one end of said container means when said container means is inserted into said second compartment to prevent said battery terminals from riding up over said contact strips.

21. The dispenser apparatus of claim 13 wherein said second vent means comprises side vent means through opposite sides of said cabinet in line with said second compartment for venting said second compartment to the atmosphere through said side vent means.

22. The dispenser apparatus of claim 13 wherein said cabinet has an open front, and a front cover over said open front, said first and second vent means comprising grill means on said front cover for venting said first and second compartments to the atmosphere through said grill means.

23. The dispenser apparatus of claim 22 wherein said second vent means further comprises side vent means through opposite sides of said front cover and cabinet in line with said second compartment for venting said second compartment to the atmosphere through said side vent means as well as through said grill means.

24. The dispenser apparatus of claim 14 further comprising a plurality of spaced apart baffles in said well in said container means.

25. Odor control product dispenser apparatus comprising a cabinet including a back wall having a partition extending forwardly therefrom intermediate the length of said back wall dividing said cabinet into first and second compartments, said first compartment containing a centrifugal fan and motor, first and second vent means for respectively venting said first and second compartments to the atmosphere, a shroud surrounding said fan, said shroud having axial inlet openings through which air is drawn by said fan through said first vent means and radial discharge opening means in said shroud for directing substantially all of the air that is forced radially outwardly by said fan into said second compartment, container means in said second compartment containing odor control product means, said container means having an open top exposing said odor control product means to the air flowing through said second compartment prior to discharge through said second vent means, and support means in said second compartment for supporting said container means with said open top facing said radial discharge opening means and in substantial alignment therewith, whereby substantially all of the air entering said second compartment through said radial discharge opening means flows past said odor control product means prior to being discharged through said second vent means.

26. The dispenser apparatus of claim 25 wherein said fan is eccentrically offset with respect to said shroud to produce a venturi effect that boosts the speed of the air being discharged by said fan through said radial discharge opening means into said second compartment.

27. The dispenser apparatus of claim 25 further comprising regulator means on said shroud for adjusting the amount of air flow being drawn through said axial inlet openings in said shroud by said fan.

28. The dispenser apparatus of claim 27 wherein said regulator means comprises an annular disk rotatably mounted on said shroud in overlying relation to said axial inlet openings, said disk having a plurality of openings therein to vary the amount of air flow through said axial inlet openings.

29. The dispenser apparatus of claim 28 wherein the size, number and location of said openings in said disk substantially correspond to the axial inlet openings in said shroud, whereby when said openings in said disk are in alignment with said axial inlet openings in said shroud, said axial inlet openings are fully open.

30. The dispenser apparatus of claim 29 wherein web-like members are provided between said openings in said disk to at least partially cover said axial inlet openings in said shroud when said openings in said disk are moved out of direct alignment with said axial inlet openings in said shroud.

31. The dispenser apparatus of claim 30 wherein said axial inlet openings in said shroud are larger than said web-like members between said openings in said disk, whereby said axial openings always remain at least partially open regardless of the rotational position of said disk relative to said axial inlet openings in said shroud.

32. The dispenser apparatus of claim 28 further comprising means on said disk and said shroud for providing a snap connection between said disk and shroud to permit attachment and removal of said disk without the use of any tools.

33. The dispenser apparatus of claim 25 wherein said shroud has a bottom wall extending forwardly from and forming a continuation of said partition, said radial discharge opening means being in said bottom wall adjacent a forward end of said partition.

34. The dispenser apparatus of claim 25 wherein said partition is a first partition and said cabinet further comprises a second another partition extending forwardly from said back wall in spaced relation from said first partition for partitioning off a portion of said first compartment, said partitions having first sides facing each other and second sides facing away from each other, and said shroud having a pair of rearwardly extending flanges overlying said second sides of said partitions.

35. The dispenser apparatus of claim 34 further comprising means on said shroud flanges and said partitions for providing a snap connection between said shroud flanges and partitions to facilitate attachment and removal of said shroud without the use of any tools.

36. The dispenser apparatus of claim 25 wherein said first compartment includes a boss extending forwardly from said back wall, said boss having a recess therein, and said motor having a cylindrical extension on one end which is slidably received in the recess in said boss.

37. The dispenser apparatus of claim 36 wherein the one end of said motor includes locating holes therein and said first compartment has pin means extending forwardly from said back wall radially outwardly of said boss which are received in the locating holes in said one end of said motor.

38. The dispenser apparatus of claim 36 wherein said first compartment has a pair of post means extending forwardly from said back wall on opposite sides of said boss, said post means having openings therein, and said motor has a motor support clip extending across a second end of said motor opposite said one end thereof, said motor support clip having an opening intermediate opposite ends thereof and spring-like fingers extending rearwardly from said opposite ends for snapping engagement into said openings in said post means for releasably mounting said motor in said first compartment, said motor having a motor shaft and shaft bearing extending through said opening in said motor support clip.

39. The dispenser apparatus of claim 25 wherein said motor has a motor shaft, and said fan includes an annular disk mounted for rotation on said motor shaft, said annular disk having a front face, and a plurality of circumferentially spaced, radially extending fan blades on said front face.

40. The dispenser apparatus of claim 39 wherein each of said fan blades has a pair of substantially parallel flat sides extending substantially perpendicular to said front face, a radial outer edge extending substantially perpendicular to said front face, a radial inner edge sloping outwardly at an angle from said front face, and a top edge extending substantially straight and parallel to said front face.

41. The dispenser apparatus of claim 25 wherein said cabinet includes an open front, and a front cover extending over said open front, said first and second vent means comprising a grill on said front cover for venting said first and second compartments to the atmosphere through said grill.

42. The dispenser apparatus of claim 41 further comprising means on said front cover and said cabinet for providing a snap connection between said front cover and cabinet to permit attachment and removal of said front cover without the use of any tools.

43. The dispenser apparatus of claim 41 wherein said second vent means further comprises side vent means through opposite sides of said cabinet in line with said second compartment for venting said second compartment to the atmosphere along opposite sides of said second compartment as well as through said grill.

44. The dispenser apparatus of claim 41 wherein said shroud has a bottom wall which forms a continuation of said partition, said radial discharge opening means being in said bottom wall adjacent a forward end of said partition, and said bottom wall having a forwardly extending flange engaging said grill.

45. The dispenser apparatus of claim 44 wherein said grill has an imperforate section intermediate opposite ends thereof, said forwardly extending flange engaging said imperforate section to isolate said first compartment from said second compartment.

* * * * *